United States Patent
Yamakawa et al.

[11] Patent Number: 5,734,063
[45] Date of Patent: Mar. 31, 1998

[54] 4-ACYLAMINOPHENYLACETYLENEALCOHOL COMPOUNDS

[75] Inventors: Katsuyoshi Yamakawa; Tadahisa Sato, both of Minami-ashigara, Japan

[73] Assignee: Fuji Photo Film Co.,Ltd., Kanagawa, Japan

[21] Appl. No.: 736,482

[22] Filed: Oct. 24, 1996

[30] Foreign Application Priority Data

Oct. 25, 1995 [JP] Japan .................... 7-277763

[51] Int. Cl.$^6$ ............ C07C 237/40; C07D 207/12; C07D 207/24; C07D 209/48

[52] U.S. Cl. ............ 548/486; 548/511; 548/513; 548/536; 548/543; 548/545; 548/547; 548/549; 548/556; 564/184; 564/186; 564/187; 564/218; 564/223

[58] Field of Search ............ 548/486, 511, 548/513, 545, 549; 564/184, 186, 187, 218, 223

[56] References Cited

U.S. PATENT DOCUMENTS 4,301,075  11/1981  Lohmann et al. .................... 260/326.5

Primary Examiner—Johann Richter
Assistant Examiner—Jane C. Oswecki
Attorney, Agent, or Firm—Sughrue, Mion, Zinn, Macpeak & Seas, PLLC

[57] ABSTRACT

The present invention provides a method for preparation of a compound of the formula (I) useful as a fog restrainer for a silver halide light-sensitive material, especially for a heat-developing light-sensitive material and a synthetic intermediate for the fog restrainer. The method makes it possible to obtain the fog restrainer in good yield and in short steps.

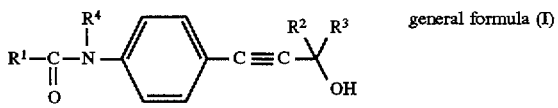

general formula (I)

wherein, $R^1$ is alkyl, cycloalkyl, or aryl, $R^2$ and $R^3$ are hydrogen atom or alkyl, $R^4$ is hydrogen atom or acyl, and $R^1$ and $R^4$ may be bonded together to form 5- or 6-membered ring.

8 Claims, No Drawings

4-ACYLAMINOPHENYLACETYLENEALCOHOL COMPOUNDS

FIELD OF THE INVENTION

The present invention relates to a synthetic intermediate for a compound which is suitable for use as a fog restrainer for a silver halide photographic light-sensitive material, especially for a heat-developing light-sensitive material and to a process for preparing the compound therefrom.

BACKGROUND OF THE INVENTION

As a processing method for a silver halide light-sensitive material, there have been developed a dry processing method by heating that provide an image easily and rapidly as compared with the conventional wet image processing method with a developer.

The heat-developing light-sensitive material is known in the art and the material and the process thereof are disclosed in U.S. Pat. No. 3,152,904, 3,301,678, 3,392,020, 3,457,075, British Patent No. 1,131,108, and 1,167,777 and Research Disclosure, June, 1978, pp. 9 to 15 (RD-17029).

Phenylacetylenes having an acylamino group, especially a secondary or tertiary alkanoylamino group at para position are useful as a fog restrainer compound.

A variety of preparation methods for phenylacetylenes have been reported, for example, in S. Patai Ed., "The chemistry of the carbon—carbon triple bond", p.755, John Wiley & Sons (1978). However, most of these synthetic methods contain a number of steps and, therefore, these methods are economically inadvantageous.

In contrast, a method which contains less steps has been reported, that is, a method comprising a coupling reaction of aryl halide and acetylene compound in the presence of palladium catalyst (e.g. Synthesis 1980, 627; ibid., 1981, 364; ibid., 1984, 728; Organometallics 12, 263 (1993): J. Org. Chem., 59, 5818(1994)).

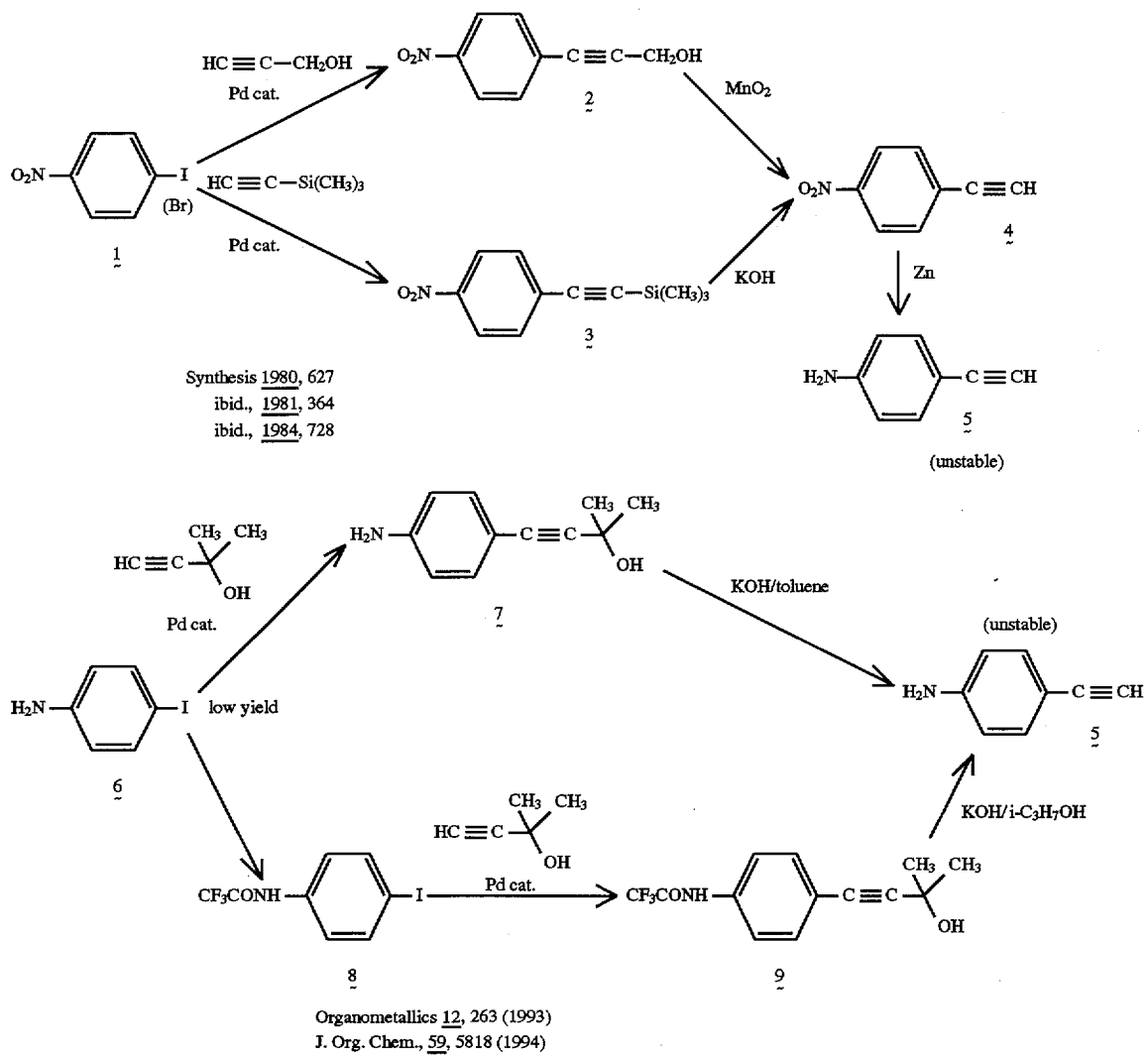

Synthesis 1980, 627
ibid., 1981, 364
ibid., 1984, 728

Organometallics 12, 263 (1993)
J. Org. Chem., 59, 5818 (1994)

4-Nitrophenylacetylene and 4-aminophenylacetylene being precursors for phenylacetylene compounds having acylamino group at para position which are objective compounds of the present invention have been prepared by the above method. However, these precursors are not suitable for synthesis in large-scale since 4-nitrophenylacetylene compound is explosive and 4-aminophenylacetylene compound is unstable.

When p-iodoanilin is reacted with acetylenealcohols in the presence of Pd catalyst, converting yield is low and, therefore, another synthetic method for 4-aminophenylacetylene has been proposed which is accomplished by use of trifluoroacetyl group as a protective group for amino group which is removed after the coupling reaction. But the method is not economically satisfied.

SUMMARY OF THE INVENTION

An object of the present invention is to provide a synthetic intermediate for p-acylaminophenylacetylene which is suitable for use as a fog restrainer for a silver halide light-sensitive material, especially for a heat-developing light-sensitive material and a method for preparing p-acylaminophenylacetylene easily and in good yield by utilizing the intermediate.

The present invention provides 4-acylaminophenylacetylenealcohol compounds represented by the following general formula (I):

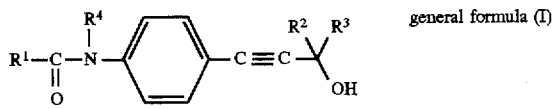

general formula (I)

wherein, $R^1$ represents secondary or tertiary alkyl, cycloalkyl or aryl group, $R^2$ represents hydrogen atom or alkyl group, $R^3$ represents alkyl group, $R^4$ represents hydrogen atom or acyl group and $R^1$ and $R^4$ may be bonded together to form 5- or 6-membered ring.

The present invention also provides a method for preparing 4-acylaminophenylacetylene compounds represented by the following general formula (II) comprising the steps of providing the compounds represented by the general formula (i) described above and reacting the compounds with tertiary amines, alkali metal hydroxides, alkali metal alkoxides or alkali metal hydrides:

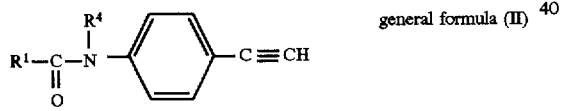

general formula (II)

wherein $R^1$ and $R^4$ have the same meaning as described in formula (I).

DESCRIPTION OF THE PREFERRED EMBODIMENTS

The compounds and the methods for preparation of the present invention will hereinafter be explained in more detail.

The compounds represented by the formula (I) will be described in more detail.

Preferably $R^1$ represents secondary or tertiary alkyl group comprising 3 to 20 carbon atoms such as isopropyl, sec-butyl, tert-butyl, tert-octyl and the like; cycloalkyl group comprising 3 to 20 carbon atoms such as cyclopropyl, cyclohexyl, adamantyl, 1-methylcyclopropyl, 1-benzylcyclopropyl and the like; or aryl group comprising 6 to 20 carbon atoms such as phenyl, naphtyl and the like.

$R^1$ represents more preferably secondary alkyl or cycloalkyl group, more preferably isopropyl or cyclohexyl group and in particular isopropyl group.

$R^2$ represents hydrogen atom or, preferably, alkyl group comprising 1 to 20 carbon atoms such as methyl, ethyl and the like, with methyl group being preferred.

$R^3$ preferably represents alkyl group comprising 1 to 20 carbon atoms such as methyl, ethyl and the like, with methyl group being preferred.

It is particularly preferred that both $R^2$ and $R^3$ represent alkyl group, especially methyl group. $R^4$ represents hydrogen atom or, preferably, acyl group comprising 1 to 20 carbon atoms such as formyl, acetyl and the like and may be bonded with $R^1$ to form 5- or 6-membered ring. Thus formed ring is preferably 5-membered ring and preferable examples thereof include phthalimide, succinimide and maleimide. In particular phthalimide is preferred.

Among the above, hydrogen atom is particularly preferred as $R^4$.

The method for preparing the compounds represented by the general formula (II) utilizing the compounds represented by the formula (I) will be described hereinafter in more detail.

The synthetic process of the present invention is shown in the following reaction scheme.

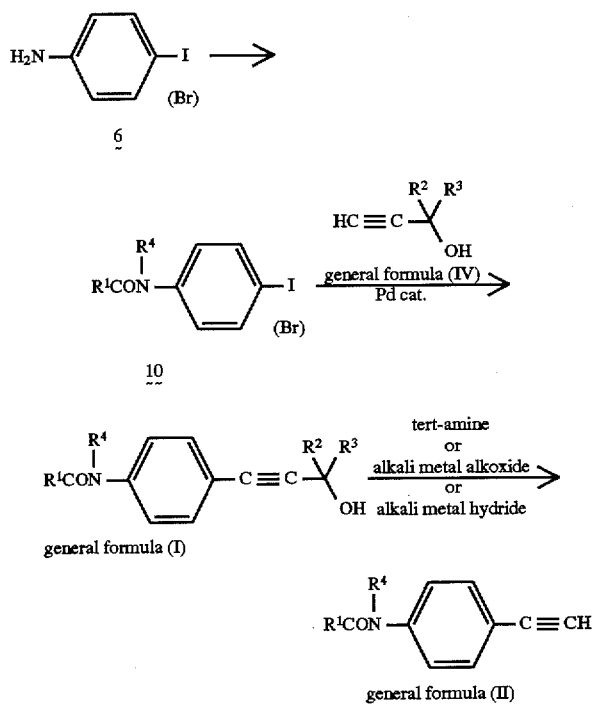

The compounds represented by the general formula (I) can be obtained in good yield from easily available p-bromoaniline or p-iodoaniline by way of compound 10. Examples of conventional solvents used for a reaction to obtain the compound 10 include amides such as acetonitrile, N, N-dimethylformamide, N, N-dimethylacetamide and the like; ethers such as diethylether, THF, dioxane and the like; esters such as ethyl acetate and the like; halogenated solvents such as methylenechloride and the like; aromatic hydrocabons such as toluene and the like. Examples of bases include pyridines such as pyridine, α-picoline, 2,6-lutidine and the like; and tertiary amines such as triethylamine and the like. It is possible to employ so called Schotten-Baumann reaction which is performed in the presence of a base such as sodium bicarbonate, sodium carbonate and sodium hydroxide and corresponding potassium salts thereof in an aqueous solution or in a mixed solvent system comprising organic solvents described above and water.

Acid chloride ($R^1$ COCl) and acid anhydride [($R^1CO)_2O$] are usually used as an acylating agent and carboxilic acids ($R^1$COOH) also may be used in combination with various condensing agents such as DCC (dicyclohexylcarbodiimide) and the like. The amount of these agents ranges from 0.5 to 1.5 equivalents, preferably 0.9 to 1.1 equivalents to the compound 6.

The method for converting the compound 10 to the compounds represented by the general formula (I) will be described below.

Acetylenealcohols represented by the general formula (IV) are inexpensively available since it is easily prepared by reacting acetylides with ketones or aldehydes. The compound represented by the formula (IV) is utilized in the amount of from 0.5 to 5 equivalents, preferably from 0.8 to 3 equivalents to the amount of compound 10. Organic bases such as diethylamine and triethylamine are generally used for the purpose of capture of acids produced. The amount of these bases is 1 to 30 equivalents, preferably 1 to 10 equivalents to the compound 10. Palladium complex having phosphine ligands (0) or (II) is usually used as palladium catalysts. Triphenylphosphine is inexpensive and is used most often as phosphine ligands, but other trivalent phosphine compounds or bidentate ligands such as di-substituted phosphinoethane also can be utilized. Most preferable palladium complex include tetrakis(triphenylphosphine) palladium(0) and bis(triphenylphosphine) palladium(II) chloride. The amount of these complexes is from $1 \times 10^{-6}$ to 1 mol equivalent, preferably $1 \times 10^{-5}$ to $1 \times 10^{-2}$ mol equivalent to the amount of the compound 10. Other phosphine compounds such as triphenylphosphine can be used in addition to the above complexes. The amount of these phosphine compounds are preferably from $1 \times 10^{-4}$ to $1 \times 10^{-2}$ mol equivalent to the amount of the compound 10.

Further, monovalent copper salts such as copper iodide can be added. The amount of the copper compounds is preferably from $1 \times 10^{-4}$ to $1 \times 10^{-1}$ mol equivalent to the amount of the compound 10.

Examples of reaction solvents include aromatic hydrocarbons such as benzene, toluene and the like; ethers such as dimethoxyethane, diglyme and the like; and amides such as dimethylformamide, dimethylacetamide and the like. It is also possible to conduct the reaction in excess amount of organic base which is used as a reactant as well as a solvent without any other solvent. The reaction temperature ranges from 0° to 150° C., preferably from 20° to 130° C., and more preferably from 20° to 90° C.

The method for preparing the compounds represented by the general formula (II) from the compounds represented by the general formula (I) will be explained below.

The compounds of formula (I) can be converted to the compounds of formula (II) by reacting with tertiary amines (e.g. triethylamine, 1,1,3,3-tetramethylguanidine(TMG), 1,5-diazabicyclo[4.3.0]-5-nonene (DBN) and 1,8-diazabicyclo[4.3.0]-7-undecene (DBU)), alkali metal hydroxides (e.g. lithium hydroxide, sodium hydroxide and potassium hydroxide) and alkali metal alkoxides (e.g. sodium methoxide, sodium ethoxide, sodium tert-butoxide, potassium tert-butoxide) and alkali metal hydrides (e.g. sodium hydride, lithium hydride and potassium hydride). Preferable tertiary amines include TMG, DBN and DBU, and more preferably DBU. Preferable alkali metal alkoxides include sodium tert-butoxide and potassium tert-butoxide.

Preferable example of alkali metal hydrides is sodium hydride.

These bases are used in the amount ranging from 0.1 to 10 equivalents, preferably 0.1 to 3 equivalents to the amount of the compound represented by the formula (I).

Examples of solvents include alcohols such as methanol, iso-propanol, tert-butanol and the like; ethers such as diethyl ether, dimethoxyethane, tetrahydrofuran and the like; amides such as N,N-dimethylacetamide (DMAC), N,N-dimethylformamide (DMF) and the like; aromatic hydrocarbons such as benzene, toluene, xylene and the like; and others such as dimethylsulfoxide, sulfolane, acetonitrile, acetone and the like.

Among the above solvents, preferred solvent is tertiary alcohol and in particular tert-butanol.

The reaction temperature ranges from 0° to 150° C., preferably from 20° to 130° C., and more preferably from 50° to 120° C.

The compounds of (I) and (II) are described in more detail hereinafter with the following embodiments. However, the compounds of the present invention are not limited thereto.

TABLE 1 general formula (1)

$$R^1-\underset{\underset{O}{\|}}{C}-\underset{\underset{}{R^4}}{N}-\text{C}_6\text{H}_4-C\equiv C-\underset{\underset{OH}{}}{\overset{R^2\ R^3}{C}}$$

| compound No. | $R^1$ | $R^2$ | $R^3$ | $R^4$ |
|---|---|---|---|---|
| (I)-1 | (CH$_3$)$_2$CH— | H | CH$_3$ | H |
| (I)-2 | (CH$_3$)$_2$CH— | CH$_3$ | CH$_3$ | H |
| (I)-3 | CH$_3$CH$_2$(CH$_3$)CH— | H | CH$_3$ | H |
| (I)-4 | CH$_3$CH$_2$(CH$_3$)CH— | CH$_3$ | CH$_3$ | H |
| (I)-5 | (CH$_3$CH$_2$)$_2$CH— | H | C$_2$H$_5$, —CHC$_4$H$_9$ | H |

TABLE 2 general formula (1)

$$R^1-\underset{\underset{O}{\|}}{C}-\underset{\underset{}{R^4}}{N}-\text{C}_6\text{H}_4-C\equiv C-\underset{\underset{OH}{}}{\overset{R^2\ R^3}{C}}$$

| compound No. | $R^1$ | $R^2$ | $R^3$ | $R^4$ |
|---|---|---|---|---|
| (I)-6 | (CH$_3$CH$_2$)$_2$CH— | CH$_3$ | CH$_3$ | H |

TABLE 2-continued general formula (1)

$$R^1-\underset{\underset{O}{\|}}{C}-\underset{R^4}{N}-C_6H_4-C\equiv C-\underset{OH}{\overset{R^2}{C}}\underset{}{\overset{R^3}{}}$$

| compound No. | $R^1$ | $R^2$ | $R^3$ | $R^4$ |
|---|---|---|---|---|
| (I)-7 | (CH$_3$CH$_2$)$_2$CH— | H | CH$_3$ | H |
| (I)-8 | (CH$_3$CH$_2$CH$_2$)$_2$CH— | CH$_3$ | CH$_3$ | H |
| (I)-9 | cyclopropyl | H | CH$_3$ | H |
| (I)-10 | cyclopropyl | CH$_3$ | CH$_3$ | H |

TABLE 3 general formula (1)

| compound No. | $R^1$ | $R^2$ | $R^3$ | $R^4$ |
|---|---|---|---|---|
| (I)-11 | cyclobutyl | H | CH$_3$ | H |
| (I)-12 | cyclobutyl | CH$_3$ | CH$_3$ | H |
| (I)-13 | cyclopentyl | H | CH$_3$ | H |
| (I)-14 | cyclopentyl | CH$_3$ | CH$_3$ | H |
| (I)-15 | cyclohexyl | H | CH$_3$ | H |
| (I)-16 | cyclohexyl | CH$_3$ | CH$_3$ | H |

TABLE 4 general formula (1)

| compound No. | $R^1$ | $R^2$ | $R^3$ | $R^4$ |
|---|---|---|---|---|
| (I)-17 | cycloheptyl | H | CH$_3$ | H |
| (I)-18 | cycloheptyl | CH$_3$ | CH$_3$ | H |
| (I)-19 | (CH$_3$)$_3$C— | H | CH$_3$ | H |
| (I)-20 | (CH$_3$)$_3$C— | CH$_3$ | CH$_3$ | H |
| (I)-21 | CH$_3$CH$_2$C(CH$_3$)$_2$— | H | CH$_3$ | H |

TABLE 5 general formula (1)

| compound No. | $R^1$ | $R^2$ | $R^3$ | $R^4$ |
|---|---|---|---|---|
| (I)-22 | CH$_3$CH$_2$C(CH$_3$)$_2$— | CH$_3$ | CH$_3$ | H |
| (I)-23 | 1-methylcyclohexyl | H | CH$_3$ | H |
| (I)-24 | 1-methylcyclohexyl | CH$_3$ | CH$_3$ | H |
| (I)-25 | 1-methylcyclopropyl | CH$_3$ | H | —CH(C$_2$H$_5$)C$_4$H$_9$ |

TABLE 5-continued general formula (1)

| compound No. | R¹ | R² | R³ | R⁴ |
|---|---|---|---|---|
| (I)-26 | CH₃ | CH₃ | CH₃ | H |
| (I)-27 | C₂H₅ | H | C₂H₅<br>\|<br>—CHC₄H₉ | H |

TABLE 6 general formula (1)

| compound No. | R¹ | R² | R³ | R⁴ |
|---|---|---|---|---|
| (I)-28 | C₂H₅ | H | C₂H₅<br>\|<br>—CHC₄H₉ | H |
| (I)-29 | 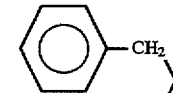C₂H₅ | CH₃ | CH₃ | H |
| (I)-30 | —CH₂— | H | CH₃ | H |
| (I)-31 | —CH₂— | CH₃ | CH₃ | H |
| (I)-32 |  | H | C₂H₅<br>\|<br>—CHC₄H₉ | H |
| (I)-33 |  | CH₃ | CH₃ | H |

TABLE 7 general formula (1)

| compound No. | R¹—C—N—<br>‖ \|<br>O R⁴ | R² | R³ |
|---|---|---|---|
| (I)-34 | phthalimido | H | CH₃ |
| (I)-35 | phthalimido | CH₃ | CH₃ |
| (I)-36 | succinimido | H | CH₃ |
| (I)-37 | succinimido | CH₃ | CH₃ |
| (I)-38 | maleimido | H | CH₃ |
| (I)-39 | maleimido | CH₃ | CH₃ |

TABLE 8 general formula (II)

R¹-C(=O)-N(R⁴)-C₆H₄-C≡CH

| compound No. | R¹ | R⁴ |
|---|---|---|
| (II)-1 | (CH₃)₂CH— | H |
| (II)-2 | CH₃CH₂(CH₃)CH— | H |
| (II)-3 | (CH₃CH₂)₂CH— | H |
| (II)-4 | (CH₃CH₂CH₂)₂CH— | H |
| (II)-5 | cyclopropyl | H |
| (II)-6 | cyclobutyl | H |
| (II)-7 | cyclopentyl | H |
| (II)-8 | cyclohexyl | H |

TABLE 9 general formula (II)

R¹-C(=O)-N(R⁴)-C₆H₄-C≡CH

| compound No. | R¹ | R⁴ |
|---|---|---|
| (II)-9 | cycloheptyl | H |
| (II)-10 | (CH₃)₃C— | H |
| (II)-11 | CH₃CH₂C(CH₃)₂— | H |
| (II)-12 | 1-methylcyclohexyl | H |
| (II)-13 | 1-methylcyclopropyl | H |
| (II)-14 | 1-ethylcyclopropyl | H |
| (II)-15 | 1-benzylcyclopropyl | H |
| (II)-16 | 1-adamantyl | H |

TABLE 10 general formula (II)

R¹-C(=O)-N(R⁴)-C₆H₄-C≡CH

| compound No. | R¹-C(=O)-N(R⁴)- |
|---|---|
| (II)-17 | phthalimido |
| (II)-18 | succinimido |

TABLE 10-continued general formula (II)

R¹—C(=O)—N(R⁴)—[phenyl]—C≡CH, with R¹—C(=O)—N(R⁴)— substituent

| compound No. | |
|---|---|
| (II)-19 | [maleimide-type structure: N-substituted with two C=O groups] |

The present invention is explained with the following working Examples in more detail.

EXAMPLE 1

Synthesis of Compound (I)-2

To a dispersion of p-iodoaniline (219.0 g, 1 mol) in acetonitrile(1000 ml) was added pyridine (81.0 ml, 1 mol). Isobutyryl chloride (100.5 ml, 1 mol) was added dropwise to the mixture over 1 hour in an ice bath. The mixture was further stirred for one hour following the addition of isobutyryl chloride and to the mixture was added water (3000 ml). Precipitated crystalline solids were collected by filtration to give N-(4-iodophenyl)isobutyramide (281.7 g, Yield: 97%).

2-Methyl-3-butyn-2-ol (21.5 g, 0.25 mol), bis (triphenylphosphine) palladium(II) chloride (0.170 g, 0.24 mol %), copper(I) iodide (0.170 g, 0.87 mol %), triphenylphosphine (0.630 g, 2.4 mol %) and triethylamine (150 ml) were added to thus obtained N-(4-iodophenyl) isobutyramide (28.9 g, 0.1 mol) and the mixture was heated under reflux for 6 hours under nitrogen atmosphere. After removal of the solvent, ethyl acetate (150 ml) was added to the residue and ethyl acetate layer was washed with water twice. Then the solvent was evaporated and the obtained oily product was purified on a silica gel column chromatography (n-hexane/ethyl acetate=1/1). Objective compound (I)-2 was crystallized from n-hexane/ethyl acetate to give a colorless crystalline solid (20.1 g, Yield : 82%).

m.p.: 175–177° C.

$^1$H—NMR (200 MHz: DMSO-d$_6$)

δ ppm 1.08 (d, 6H, J=8.7 Hz), 1.46 (s, 6H), 2.4–2.6 (m, 1H), 5.40 (s, 1H), 7.29 (d, 2H, J=9.1 Hz), 7.60 (d, 2H, J=9.1 Hz), 9.93 (s, 1H).

EXAMPLE 2

Synthesis of Compound (I)-1

Compound (I)-1 was obtained by repeating the same procedure as Example 1 except that the same amount (mol) of 3-butyn-2-ol was used instead of 2-methyl-3-butyn-2-ol (19.4 g, Yield: 89%).

EXAMPLE 3

Synthesis of Compound (I)-20

Compound (I)-20 was obtained by repeating the same procedure as Example 1 except that the same amount (mol) of pivaloyl chloride was used instead of isobutyryl chloride (19.2 g, Yield: 85%).

EXAMPLE 4

Synthesis of Compound (II)-1 From Compound (I)-2

To a compound (I)-2 (24.6 g, 0.1 mol) were added tert-butanol (100 ml) and potassium tert-butoxide (2.40 g, 0.02 mol). The mixture was heated for 6 hours with evaporating solvent step by step to remove acetone produced. After removal of solvent, the mixture was cooled to room temperature and isopropanol (100 ml) and water (100 ml) were subsequently added. The mixture was stirred for one hour in an ice bath and crystallized solid was collected by filtration to give the objective compound (II)-1 as a colorless crystalline solid (15.6 g, Yield: 83%).

m.p.: 156–158° C.

$^1$H—NMR (200 MHz: CDCl$_3$)

δppm 1.25 (d, 6H, J=8.7 Hz), 2.4–2.6 (m, 1H), 3.06 (s, 1H), 7.44 (d, 2H, J=9.1 Hz), 7.51 (d, 2H, J=9.1 Hz),

EXAMPLE 5

Synthesis of Compound (II)-1 by Reacting Compound (I)-2 with Various Bases

To the compound (I)-2 (1.23 g) (5 mmol) were added solvent 5 ml and a base, and the mixture was heated under reflux for 3 hours under nitrogen atmosphere. The reaction mixture was quantitatively determined by liquid chromatography (254 nm) and results are shown in Table 11.

Table 11

| Base (eq. mol to (I)-2) | | Solvent | Yield of (II)-1 (%) |
|---|---|---|---|
| NaH | (1.1) | toluene | 73.4 |
| NaOH | (1.1) | toluene | 43.7 |
| KOH | (1.1) | toluene | 45.1 |
| t-BuOK | (1.1) | toluene | 33.9 |
| NaOCH$_3$ | (1.1) | toluene | 49.5 |
| K$_2$CO$_3$ | (1.1) | toluene | 0 |
| DBU | (1.1) | toluene | 15.0 |
| NaH | (1.1) | THF | 81.9 |
| NaH | (2.2) | THF | 27.5 |
| t-BuOK | (1.1) | THF | 83.3 |
| t-BuOK | (2.2) | THF | 89.3 |
| NaOCH$_3$ | (1.1) | THF | 69.8 |
| NaH | (0.2) | THF | 74.2 |
| t-BuOK | (0.2) | THF | 81.8 |
| NaH | (1.1) | i-C$_3$H$_7$OH | 79.6 |
| NaOH | (1.1) | i-C$_3$H$_7$OH | 59.8 |
| KOH | (1.1) | i-C$_3$H$_7$OH | 70.6 |
| t-BuOK | (1.1) | i-C$_3$H$_7$OH | 66.3 |
| t-BuOK | (0.2) | i-C$_3$H$_7$OH | 87.2 |
| NaH | (0.2) | i-C$_3$H$_7$OH | 84.7 |
| NaH | (1.1) | t-C$_4$H$_9$OH | 84.0 |

Table 11-continued

| Base (eq. mol to (I)-2) | | Solvent | Yield of (II)-1 (%) |
|---|---|---|---|
| NaH | (0.2) | t-C$_4$H$_9$OH | 86.3 |
| t-BuOK | (1.1) | t-C$_4$H$_9$OH | 88.8 |
| t-BUOK | (0.2) | t-C$_4$H$_9$OH | 94.2 |
| t-BuONa | (0.2) | t-C$_4$H$_9$OH | 91.5 |

As shown in Table 11, good yield was obtained when sodium tert-butoxide or potassium tert-butoxide was used and tert-butanol was used as a solvent.

According to the present invention, a fog restrainer for a heat-developing light-sensitive material is prepared in short steps and and in good yield.

What is claimed is:

1. 4-Acylaminophenylacetylenealcohol compound represented by the following formula (I):

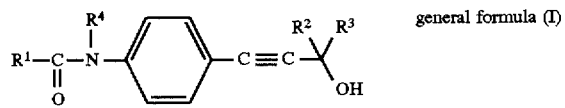

general formula (I)

wherein, $R^1$ represents a secondary or tertiary alkyl, cycloalkyl or aryl group, $R^2$ represents a hydrogen atom or an alkyl group, $R^3$ represents an alkyl group, $R^4$ represents a hydrogen atom or an acyl group and $R^1$ and $R^4$ may be bonded together to form a 5- or 6-membered ring.

2. A compound according to claim 1, wherein $R^1$ represents a $C_{3-20}$ secondary alkyl, a $C_{3-20}$ tertiary alcohol, a $C_{3-20}$ cycloalkyl or a $C_{6-20}$ aryl group.

3. A compound according to claim 2, wherein $R^1$ represents $C_{3-20}$ secondary alkyl group or a $C_{3-20}$ cycloalkyl group.

4. A compound according to claim 1, wherein $R^2$ represents a hydrogen atom or a $C_{1-20}$ alkyl group and $R^3$ represents a $C_{1-20}$ alkyl group.

5. A compound according to claim 4, wherein both $R^2$ and $R^3$ represent a methyl group.

6. A compound according to claim 1, wherein $R^4$ represents a hydrogen atom or a $C_{1-20}$ acyl group.

7. A compound according to claim 6, wherein $R^4$ represents a hydrogen atom.

8. A compound according to claim 1, wherein $R^1$ and $R^4$ are bonded together to form a 5-membered ring selected from the group consisting of phthalimide, succinimide and maleimide.

* * * * *